US009085786B2

(12) United States Patent
Hauer et al.

(10) Patent No.: US 9,085,786 B2
(45) Date of Patent: Jul. 21, 2015

(54) PROCESS FOR THE PRODUCTION OF POLYAMINES

(75) Inventors: Bernhard Hauer, Fussgönheim (DE); David Karim Engelmark Cassimjee, Stockholm (SE); Per Berglund, Stockholm (SE)

(73) Assignee: BASF SE (DE)

( * ) Notice: Subject to any disclaimer, the term of this patent is extended or adjusted under 35 U.S.C. 154(b) by 378 days.

(21) Appl. No.: 13/505,675

(22) PCT Filed: Oct. 29, 2010

(86) PCT No.: PCT/EP2010/066449
§ 371 (c)(1),
(2), (4) Date: May 2, 2012

(87) PCT Pub. No.: WO2011/051433
PCT Pub. Date: May 5, 2011

(65) Prior Publication Data
US 2012/0225932 A1   Sep. 6, 2012

(30) Foreign Application Priority Data
Nov. 2, 2009 (EP) .................................... 09174796

(51) Int. Cl.
| C12N 13/00 | (2006.01) |
| C12P 13/00 | (2006.01) |
| A61K 8/84  | (2006.01) |
| A61Q 19/00 | (2006.01) |
| C08G 73/02 | (2006.01) |
| D21H 17/56 | (2006.01) |
| C12N 9/06  | (2006.01) |
| A61K 47/18 | (2006.01) |
| D21C 9/08  | (2006.01) |
| D21H 21/02 | (2006.01) |

(52) U.S. Cl.
CPC ............... *C12P 13/001* (2013.01); *A61K 8/84* (2013.01); *A61Q 19/00* (2013.01); *C08G 73/0206* (2013.01); *C08G 73/0213* (2013.01); *D21H 17/56* (2013.01); *A61K 47/18* (2013.01); *C12N 9/0014* (2013.01); *D21C 9/08* (2013.01); *D21H 21/02* (2013.01)

(58) Field of Classification Search
CPC ......... A61K 8/84; A61K 47/18; A61Q 19/00; C08G 73/2006; C08G 73/2013; C12P 13/001; D21H 17/56; D21H 21/02; D21C 9/08; C12N 9/0014
See application file for complete search history.

(56) References Cited

U.S. PATENT DOCUMENTS

| 4,048,148 A | 9/1977 | Morgan |
| 6,596,520 B1 | 7/2003 | Friedrich et al. |

| 2003/0224028 A1 | 12/2003 | Galey |
| 2008/0069969 A1 | 3/2008 | Hatanaka et al. |
| 2009/0181948 A1* | 7/2009 | Sasho et al. .............. 514/217.04 |

FOREIGN PATENT DOCUMENTS

| EP | 1 069 183 A2 | 1/2001 |
| EP | 1149849 A1 | 10/2001 |
| EP | 1364641 A1 | 11/2003 |

OTHER PUBLICATIONS

Grunwald et al. J. Am. Chem. Soc. (1986) 108: 6732-6734.*
Witkowski et al. Biochemistry (1999) 38: 11643-11650.*
Whisstock et al. Quarterly Rev. Biophysics (2003) 36(3): 307-340.*
Chica et al. Current Opinion Biotechnology (2005) 16: 378-384.*
Andersson, L, et al., "A General Method of α-Aminoaldehyde Synthesis Using Alcohol Dehydrogenase", Analytical Biochemistry, vol. 124, (1982), pp. 150-157.
Belenkov, A., et al., "Polyethyleneimine Grafted with Pluronic P85 Enhances Ku86 Antisense Delivery and the Ionizing Radiation Treatment Efficacy in vivo", Gene Therapy, vol. 11, (2004), pp. 1665-1672.
De Lathouder, K.M., et al., "Polyethyleneimine (PEI) Functionalized Ceramic Monoliths as Enzyme Carriers: Preparation and Performance", Journal of Molecular Catalysis B: Enzymatic, vol. 50, (2008), pp. 20-27.
Grunwald, P, et al., "Application of Polyethylene Imine as Carrier Material for Enzyme Immobilization", Naturwissenschafter, vol. 68, (1981), pp. 525-526.
Jeong, J.H., et al., "A New Antisense Oligonucleotide Delivery System Based on Self-Assembled ODN-PEG Hybrid Conjugate Micelles", Journal of Controlled Release, vol. 93, (2003), pp. 183-191.
Kaur, N., et al., "Designing the Polyamine Pharmacophore: Influence of N-Substituents on the Transport Behavior of Polyamine Conjugates", J. Med. Chem, vol. 51, (2008), pp. 2551-2560.
Lungwitz, U., et al., "Polyethylenimine-Based Non-Viral Gene Delivery Systems", European Journal of Pharmaceutics and Biopharmaceutics, vol. 60, (2005), pp. 247-266.
Matos, J. R., et al., "Enantioselectivity of Alcohol Dehydrogenase-Catalyzed Oxidation of 1,2-Diols and Aminoalcohols", Bioorganic Chemistry, vol. 13, (1985), pp. 121-130.
Patel, R. N., et al., "Microbial Oxidation of Methanol: Properties of Crystallized Alcohol Oxidase from a Yeast, *Pichia* sp.", Archives of Biochemistry and Biophysics, vol. 210, No. 2, (1981), pp. 481-488.
Riebel, B. R., et al., "Cofactor Regeneration of Both NAD$^+$ from NADH and NADP$^+$ from NADPH:NADH Oxidase from *Lactobacillus sanfranciscensis*", Adv. Synth. Catal., vol. 345, (2003), pp. 707-712.
Ingberman A. K., et al., Database CAPLUS, Accession No. 1961-7629, (1958).

* cited by examiner

*Primary Examiner* — Susan Hanley
(74) *Attorney, Agent, or Firm* — Drinker Biddle & Reath LLP

(57) ABSTRACT

The present invention relates to a process for the production of a polyamine involving the use of enzymes; in particular to a process performed in aqueous environment; to the polyamines produced by said method; as well as the use of said polyamines for manufacturing paper, for immobilizing enzymes, or for preparing pharmaceutical or cosmetical compositions. The invention also relates to a novel method for in situ regeneration of cofactors NAD(P)$^+$.

16 Claims, 4 Drawing Sheets

SEQUENCE LISTING

<160> NUMBER OF SEQ ID NOS: 2

<210> SEQ ID NO 1
<211> LENGTH: 374
<212> TYPE: PRT
<213> ORGANISM: Equus caballus

<400> SEQUENCE: 1

Met Ser Thr Ala Gly Lys Val Ile Lys Cys Lys Ala Ala Val Leu Trp
1               5                   10                  15

Glu Gln Lys Lys Pro Phe Ser Ile Glu Glu Val Glu Val Ala Pro Pro
                20                  25                  30

Lys Ala His Glu Val Arg Ile Lys Met Val Ala Ala Gly Ile Cys Arg
            35                  40                  45

```
Ser Asp Asp His Val Val Ser Gly Thr Leu Val Ala Pro Leu Pro Val
    50              55                  60

Ile Ala Gly His Glu Ala Ala Gly Ile Val Glu Ser Ile Gly Glu Gly
65              70                  75                  80

Val Thr Thr Val Arg Pro Gly Asp Lys Val Ile Pro Leu Phe Ile Pro
                85                  90                  95

Gln Cys Gly Lys Cys Ser Val Cys Lys His Pro Glu Gly Asn Leu Cys
                100                 105                 110

Leu Lys Asn Leu Ser Met Pro Arg Gly Thr Met Gln Asp Gly Thr Ser
            115                 120                 125

Arg Phe Thr Cys Arg Gly Lys Pro Ile His His Phe Leu Gly Thr Ser
    130                 135                 140

Thr Phe Ser Gln Tyr Thr Val Val Asp Glu Ile Ser Val Ala Lys Ile
145                 150                 155                 160

Asp Ala Ala Ser Pro Leu Glu Lys Val Cys Leu Val Gly Cys Gly Phe
                165                 170                 175

Ser Thr Gly Tyr Gly Ser Ala Val Lys Val Ala Lys Val Thr Gln Gly
            180                 185                 190

Ser Thr Cys Ala Val Phe Gly Leu Gly Gly Val Gly Leu Ser Val Ile
    195                 200                 205

Met Gly Cys Lys Ala Ala Gly Ala Ala Arg Ile Ile Gly Val Asp Ile
    210                 215                 220

Asn Lys Asp Lys Phe Ala Lys Ala Lys Glu Val Gly Ala Thr Glu Cys
225                 230                 235                 240

Val Asn Pro Gln Asp Tyr Lys Lys Pro Ile Gln Glu Val Leu Thr Glu
                245                 250                 255

Met Ser Asn Gly Gly Val Asp Phe Ser Phe Glu Val Ile Gly Arg Leu
            260                 265                 270

Asp Thr Met Val Ala Ala Leu Ser Cys Cys Gln Glu Ala Tyr Gly Val
    275                 280                 285

Ser Val Ile Val Gly Val Pro Pro Asp Ser Gln Asn Leu Ser Met Asn
290                 295                 300

Pro Met Leu Leu Leu Ser Gly Arg Thr Trp Lys Gly Ala Ile Phe Gly
305                 310                 315                 320

Gly Phe Lys Ser Lys Asp Ser Val Pro Lys Leu Val Ala Asp Phe Met
                325                 330                 335

Ala Lys Lys Phe Ala Leu Asp Pro Leu Ile Thr His Val Leu Pro Phe
                340                 345                 350

Glu Lys Ile Asn Glu Gly Phe Asp Leu Leu Arg Ser Gly Lys Ser Ile
            355                 360                 365

Arg Thr Ile Leu Thr Phe
    370

<210> SEQ ID NO 2
<211> LENGTH: 33
<212> TYPE: PRT
<213> ORGANISM: Pichia pastoris
<220> FEATURE:
<221> NAME/KEY: PEPTIDE
<222> LOCATION: (1)..(33)
<223> OTHER INFORMATION: Partial sequence

<400> SEQUENCE: 2

Met Ala Ile Pro Glu Glu Phe Asp Ile Leu Val Leu Gly Gly Gly Ser
1               5                   10                  15
```

```
Ser Gly Ser Cys Ile Ala Gly Arg Leu Ala Asn Leu Asp His Ser Leu
                20              25              30
Lys
```

PROCESS FOR THE PRODUCTION OF POLYAMINES

CROSS-REFERENCE TO RELATED APPLICATIONS

This application is a national stage application (under 35 U.S.C. §371) of PCT/EP2010/066449, filed Oct. 29, 2010, which claims benefit of European Application No. 09174796.4, filed Nov. 2, 2009.

The present invention relates to a process for the production of a polyamine involving the use of enzymes; in particular to a process performed in aqueous environment; to the polyamines produced by said method; as well as the use of said polyamines for manufacturing paper, for immobilizing enzymes, or for preparing pharmaceutical or cosmetical compositions. The invention also relates to a novel method for in situ regeneration of cofactors $NAD(P)^+$.

BACKGROUND OF THE INVENTION

Polyamines, such as PEI (poly ethylene imine), are cationic polymers with a vast variety of applications. PEI and derivatives thereof are used in e.g. pulp and paper production to overcome manufacturing problems caused by resins and mechanical pulp extractives (Mönch D, Stange A, Linhart F, *Advanced Product Concepts for Concomitant Elimination and Increased Efficiency of Paper Manufacture*, Wochenblatt für Papierfabrikation 1996, 124:889-892, 894-895). The charged nature of the polymer also makes it useful for immobilization of e.g. enzymes (Grunwald P, Freder R, Gunsser W, *Application of polyethylene imine as carrier material for enzyme immobilization* Naturwissenschaften 1981, 68:525-526); (de Lathouder K M, van Benthem D T J, Wallin S A, Mateo C., Fernandez Lafuente R, Guisan J M, Kapteijn F, Moulijn J A, *Polyethyleneimine (PEI) functionalized ceramic monoliths as enzyme carriers: Preparation and performance* Journal of Molecular Catalysis B: Enzymatic 2008, 50:20-27).

Recently advances have been made in gene delivery where PEI, sometimes in combination with PEG, has shown to increase the cell penetration of DNA/RNA (Lung-witz U, Breunig M, Blunk T, Göpferich A, *Polyethylenimine-based non-viral gene delivery systems* European Journal of Pharmaceutics and Biopharmaceutics 2005, 60:247-266); (Belenkov A I, Alakhov V Y, Kabanov A V, Vinogradov S V, Panasci L C, Monia B P, Chow T Y. *Polyethyleneimine grafted with pluronic P85 enhances Ku86 antisense delivery and the ionizing radiation treatment efficacy in vivo.* Gene Therapy 2004, 11:1665-1672.); (Jeong J H, Kim S W, Park T G. *A new antisense oligonucleotide delivery system based on self-assembled ODN-PEG hybrid conjugate micelles.* Journal of Controled Release. 2003, 93:183-191.) This is a very promising application since the concept of ADN (antisense oligonucleotides) was introduced, and received the Noble prize in the Year 2006. Successful delivery of an anticoding gene would cure a plethora of diseases such as HIV, cancer, autoimmune responses etc. Further therapeutic applications of polyamines include relief of symptoms related to skin diseases and chemotherapy.

The currently available polyamines such as PEI and dendrimers are synthesized in organic solvent. The conventional polymerization of ethylene imine is based on ring opening, thus limiting the length of the repetitive unit to two carbons between the nitrogen atoms.

The problem to be solved by the present invention is, therefore, to provide a method of preparing polyamines which may be performed in aqueous environment, and which is not limited to $C_2$-building blocks.

SUMMARY OF THE INVENTION

The above problem was solved by providing a novel synthesis method of polyamines which may be performed in aqueous medium and which is based on the use of certain enzymes as further defined in the attached claims.

In particular, new methods for synthesizing polyamines are provided, schematically depicted in FIGS. 1 and 2. An aminoalcohol, e.g. 3-amino-1-propanol, is oxidized in aqueous environment to an aminoaldehyde by the action of an alcohol dehydrogenase such as Horse Liver Alcohol Dehydrogenase (HLADH), using $NAD^+$/NADH as cofactor (FIG. 1) or an alcohol oxidase making use of molecular oxygen as electron aczeptor (FIG. 2). The aminoaldehydes thus formed react spontaneously to imines at moderately acidic pH, thus forming polyimines. By reduction, for example with sodium cyanoborohydride, said polyimine is then converted into a polyamine. The repetitive unit in the polymer may have two or more carbon atoms between the nitrogens, may have functional groups, and be a chiral compound, only limited by the enzyme's capability of accepting the starting aminoalcohol as a substrate. There are many alcohol dehydrogenases and alcohol oxidases found in nature, all with different substrate specificity and/or activity.

To support a complete conversion of substrate applying a method for cofactor regeneration is of advantage. To date the regeneration of $NAD^+$ has been a problem; one method utilizes the enzyme NADH-oxidase which is a rather expensive substance (Riebel B R, Gibbs P R, Wellborn W B, Bommarius A S, *Cofactor Regeneration of both NAD+ from NADH and NADP+ from NADPH:NADH Oxidase from Lactobacillus sanfranciscensis* Advanced Synthesis & Catalysis 2003, 345: 707-712).

By the present invention, a new and simple method is presented based on the spontaneous hydrolysis of vinyl acetate, which method may be coupled with the enzymatic olymerization reaction Where alcohol oxidase is used the formed hydrogen peroxide is rapidly converted to water and oxygen by coupling the reaction with the catalytic activity of an oxidizing enzyme, in particular catalase, thereby shifting the reaction equilibrium further to the side of the aldehyde, and thus supporting a complete conversion of the substrate.

PARTICULAR EMBODIMENTS OF THE INVENTION

Figure 1:
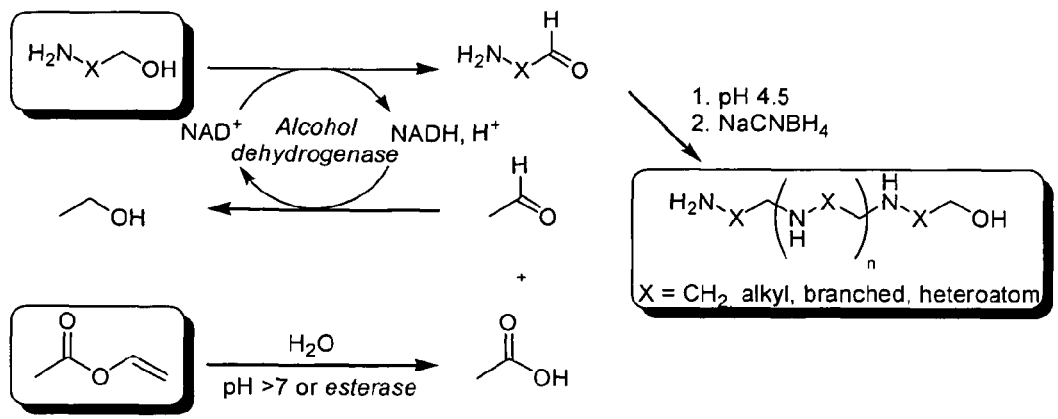
FIG. 1: Schematic representation of polyamine synthesis, catalyzed by an alcohol dehydrogenase. The pH is lowered to pH 4.5 allowing polyimine formation. This is then followed by reduction of the polyimine by cyanoborohydride. Recycling of the cofactor utilizes formed acetaldehyde in situ which is formed after spontaneous hydrolysis of vinyl acetate at alkaline pH or, alternatively using an esterase.

1. In a first embodiment, the present invention provides a process, in particular performed in an aqueous reaction medium, for the production of a polyamine of the general formula (4)

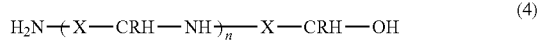

(4)

wherein n is an integer of at least 1;

residues X independently of each other represent a linear or branched, saturated or unsaturated hydrocarbylene residue, optionally carrying one or more identical or different heteroatoms selected from N, O, and S;

residues R independently of each other represent a hydrogen atom or a linear or branched, saturated or unsaturated, hydrocarbyl residue, optionally carrying one or more heteroatoms selected from N, O, and S; and wherein the terminal $H_2N-$ and $HO-CH_2-$ groups may be condensed to form an intramolecular amino linkage, comprising the steps of a) enzymatically oxidizing an aminoalcohol of the general formula (1), which may be chiral or non-chiral, and may be applied in optically pure form or as a mixture of isomers, to the corresponding aminoaldehyde of the formula (2)

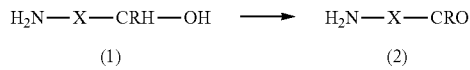

wherein X and R are as defined above;

b) allowing the aminoaldehyde of the formula (2) to polymerize to a polyimine (3),

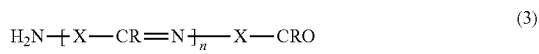

(3)

wherein X, R and n are as defined above; and c) reducing, preferably chemically, the polyimine of the formula (3) to the corresponding polyamine of the formula (4).

2. The process according to embodiment 1, wherein the aminoalcohol of step a) is a compound of the formula (1), wherein $X=-CH_2-CH_2-$.

3. The process according to embodiment 1 or 2, wherein the enzyme of step a) is selected dehydrogenases and oxidases in particular, alcohol dehydrogenase E.C. 1.1.1.1, alcohol dehydrogenase (NADP+) 1.1.1.2, allyl-alcohol dehydrogenase E.C. 1.1.1.54, alcohol dehydrogenase [NAD(P)+] E.C. 1.1.1.71, aryl-alcohol dehydrogenase E.C. 1.1.1.90, aryl-alcohol dehydrogenase (NADP+) E.C. 1.1.1.91, 3-hydroxybenzyl-alcohol dehydrogenase E.C. 1.1.1.97, perillyl-alcohol dehydrogenase E.C. 1.1.1.144, long-chain-alcohol dehydrogenase E.C. 1.1.1.192, coniferyl-alcohol dehydrogenase E.C. 1.1.1.194, cinnamyl-alcohol dehydrogenase E.C. 1.1.1.195, cyclohexanol dehydrogenase E.C. 1.1.1.245, 4-(hydroxymethyl)benzenesulfonate dehydrogenase E.C. 1.1.1.257, 3-methylbutanal reductase E.C. 1.1.1.265, S-(hydroxymethyl)glutathione dehydrogenase E.C. 1.1.1.284, alcohol dehydrogenase (acceptor) E.C. 1.1.99.8, polyvinyl-alcohol dehydrogenase (acceptor) E.C. 1.1.99.23, formaldehyde dehydrogenase (glutathione) E.C. 1.2.1.1 and alcohol oxidase, E.C. 1.1.3.13, aryl-alcohol oxidase E.C. 1.1.3.7, secondary-alcohol oxidase E.C. 1.1.3.18, long-chain-alcohol oxidase E.C. 1.1.3.20, polyvinyl-alcohol oxidase E.C. 1.1.3.30, vanillyl-alcohol oxidase E.C. 1.1.3.38, 4. The process of embodiment 3, wherein the enzyme is a horse liver alcohol dehydrogenase (HLADH) and has the polypeptide sequence of SEQ ID NO:1 or an alcohol oxidase having a polypeptide sequence of SEQ ID NO:2; or a mutant or variant thereof having a sequence identity of at least 60% to a sequence of SEQ ID NO: 1 or 2.

5. The process according to embodiment 3 or 4, wherein in step a) $NAD^+$ is used as a cofactor for the oxidation if an alcohol dehydrogenase is applied; or the reaction is performed aerobically if an alcohol oxidase is applied.

6. The process according to embodiment 5, wherein the $NAD^+$ cofactor is regenerated enzymatically by the reduction of an aldehyde or ketone to the corresponding alcohol by the same dehydrogenase enzyme.

7. The process of embodiment 5, wherein the aldehyde or ketone are formed by the hydrolysis of an activated ester.

8. The process according to one of the preceding embodiments, wherein the chemical reduction step c) is performed in the presence of $NaBH_3CN$ or $Pd/H_2$.

9. The process according to one of the preceding embodiments, wherein a polyamine in the molecular range of Mn=100 to 7,000,000, 200 to 1,000,000, 250 to 500,000, 300 to 100,000, 350 to 50,000, 400 to 10,000 or 450 to 5,000 is obtained. Particular Mn ranges are 500 to 4,000 or 500 to 3,000 or 500 to 2,000.

10. The process according to anyone of the preceding embodiments, wherein step b) is performed preferably in an aqueous medium having a pH allowing the formation of polyimine, in particular a pH in the range of 3.5 to 6 or 4 to 5.

11. The process according to one of the preceding embodiments, wherein step a) is performed in an aqueous medium having a pH in the range of 6 to 10 as for example 7 to 9 or 7.5 to 8.

12. The process according to one of the preceding embodiments, wherein the enzyme is used in dissolved, dispersed or immobilized form.

13. A polyamine obtainable by a process of any one of the preceding embodiments.

14. The use of an enzyme as defined in any one of the embodiments 3 and 4 for preparing a polyamine.

15. The use of a polyamine as obtainable by a process of any one of the embodiments 1 to 12 for manufacturing paper; for immobilizing enzymes, or for preparing pharmaceutical or cosmetic compositions.

16. The use of embodiment 15, wherein the pharmaceutical composition is selected from compositions for improving the cell penetration of DNA and/or RNA; ointments for treatment of skin diseases; compositions for treating the side effects of chemotherapy; drug delivery compositions, in particular localized slow release agents.

17. A method of regenerating $NAD(P)^+$ as produced during a dehydrogenase catalyzed oxidation reaction of a first substrate S1 of said enzyme to form a first, oxidized product P1, which method comprises the regeneration of NAD(P)$^+$ by coupling said dehydrogenase catalyzed oxidation reaction a second simultaneously proceeding dehydrogenase catalyzed reduction reaction of a second substrate S2 of said enzyme, different from S1 and P1, to form a second reduced, product P2, different from P1 and S1, wherein said substrate S2 is produced in situ from a precursor molecule PrS2 and which precursor molecule PrS2 decomposes spontaneously or via the action of a second enzyme different from said dehydrogenase.

18. The method of embodiment 17, wherein the dehydrogenase is an alcohol dehydrogenase (ADase).

19. The method of embodiment 17 or 18, wherein the PrS2 molecule is a vinylester of a carboxylic acid, which upon chemical of enzymatic hydrolysis is decomposed to the corresponding carboxylic acid and acetaldehyde as the second substrate S2.

20. The method of any one of the embodiments 17 to 19, wherein the first substrate S1 is an alcohol oxidizable by said ADase.

21. The method of embodiment 20, wherein the alcohol is an amino alcohol of the above identified formula (1).

22. The method of any one of the embodiments 18 to 21, wherein the regeneration reaction is performed in an aqueous medium.

FURTHER EMBODIMENTS OF THE INVENTION

1. Definitions

Unless otherwise stated the following definitions shall apply:

In compounds of the above formulae (1) to (4):

The parameter n is an integer of at least 1, as for example 1 to 10,000, 1 to 5,000, 2 to 1,000, 3 to 800, 4 to 600, 5 to 500, 10 to 200, 15 to 100, 20 to 80 or 30 to 60, in particular 2 to 100, 3 to 50, 4 to 30, 5 to 20.

Residues X are the same or different and represent a linear or branched; saturated or unsaturated, optionally substituted hydrocarbylene residue, optionally carrying one or more, like 1, 2 or 3, heteroatoms selected from N, O, and S in its chain; particular residues X are linear $C_1$-$C_{10}$ or $C_1$-$C_5$, as for example $C_1$, $C_2$, $C_3$, $C_4$ or $C_6$ hydrocarbylene residues or branched $C_3$-$C_{10}$ or $C_3$-$C_6$, as for example $C_3$, $C_4$, $C_6$, or $C_6$ hydrocarbylene residues, optionally carrying one ore two heteroatom, in particular one O or S atom thus forming an ether or thioether group Residues R are the same or different and a linear or branched; saturated or unsaturated, optionally substituted hydrocarbyl residue, optionally carrying one or more heteroatoms selected from N, O, and S; like linear $C_1$-$C_{10}$ or $C_1$-$C_5$, as for example $C_1$, $C_2$, $C_3$, $C_4$ or $C_5$, hydrocarbyl residues or branched $C_3$-$C_{10}$ or $C_3$-$C_6$, as for example $C_3$, $C_4$, $C_5$, or $C_6$ hydrocarbyl residues, Optional substituents of X and R are selected from hydroxy, mercapto, amino, and halogen, like F, CI, Br.

Linear $C_1$-$C_{10}$ hydrocarbyl residues comprise methyl, ethyl, propyl, butyl, pentyl, hexyl, heptyl, octyl, nonyl and decyl. Branched $C_3$-$C_{10}$ hydrocarbyl residues are, for example, isopropyl, isobutyl, isopentyl, 2,2-dimethylpropyl, isohexyl, 3-methylpentyl, 2,2-dimethylbutyl 2,3-dimethylbutyl, isoheptyl, 3-methylhexyl, 2,2-dimethylpentyl, 2,3-dimethylpentyl, 2,4-dimethylpentyl, 2,2,3-trimethylbutyl, isooctyl, 3-methylheptyl, 4-methylheptyl, 2,2-dimethylhexyl, 2,4-dimethylhexyl, 2,5-dimethylhexyl, 2,2,3-trimethylpentyl, 2,2,4-trimethylpentyl, 2,2,5-trimethylpentyl und isononyl.

Linear $C_1$-$C_{10}$ hydrocarbylene residues comprise methylene, ethylene, propylene, butylene, pentylene, hexylene, heptylene, octylene, nonylene and decylene. Branched $C_3$-$C_{10}$ hydrocarbyene residues are, for example, isopropylene, isobutylene, isopentylene, 2,2-dimethylpropylene, isohexylene, 3-methylpentylene, 2,2-dimethylbutylene 2,3-dimethylbutylene, isoheptylene, 3-methylhexylene, 2,2-dimethylpentylene, 2,3-dimethylpentylene, 2,4-dimethylpentylene, 2,2,3-trimethylbutylene, isooctyl, 3-methylheptylene, 4-methylheptylene, 2,2-dimethylhexylene, 2,4-dimethylhexylene, 2,5-dimethylhexylene, 2,2,3-trimethylpentylene, 2,2,4-trimethylpentylene, 2,2,5-trimethylpentylene und isononylene.

Unless otherwise stated the expression "aminoalkanol" or "aminoaldehyde" or "polyamine" or "polyimine" as used according to the present invention refer to such compound in its uncharged or charged form, like ammonium salts, or mixtures charged and non-charged forms. Ammonium salts may be formed with conventional counter-ions, like hydroxide or of halogenide anions, like F$^-$, Cl$^-$, Br$^-$.

An "intermediary product" is understood as a product, which is transiently or continuously formed during a chemical or biochemical process, in a not necessarily analytically directly detectable concentration. Said "intermediary product" may be removed or isolated from said process of directly further converted by a second, chemical or biochemical reaction.

As used herein, a "substantially pure" protein or enzyme means that the desired purified protein is essentially free from contaminating cellular components, as evidenced by a single band following polyacrylamide-sodium dodecyl sulphate gel electrophoresis (SDS-PAGE). The term "substantially pure" is further meant to describe a molecule, which is homogeneous by one or more purity or homogeneity characteristics used by those of skill in the art. For example, a substantially pure Protein or enzyme will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of said protein or enzyme with other compounds. In addition, the term is not meant to exclude fusion proteins comprising said protein or enzyme optionally isolated from a recombinant host.

"Condensed" or "condensation" refers to the intermolecular or in particular intramolecular formation of a chemical bond and the simultaneous formation of a low molecular chemical by-product, in particular water.

An "enzymatic" reaction refers to a reaction performed under the catalytic action at least one enzyme, either in crude, i.e. non-purified or substantially purified form, or in the presence of whole microorganisms, expressing said enzyme and optionally shedding said enzyme into the extracellular space.

An "aqueous reaction medium" is a liquid medium, the liquid constituents essentially consisting of water or mixtures of water with a at least one organic liquid, which may at least partially, or in particular completely be mixed with water, like low molecular weight alcanols, like methanol or ethanol, or ethers, like THF, or others like DMSO, dioxane, acetonitrile. In particular, the proportion of the organic constituent may be below 80 vol.-%, in particular, below 50, 40, 30, 20, 10 or 5 vol.-%, based on the total volume of the mixture. In particular, amount and type of the organic constituent are such that a reaction according to the present invention is not negatively affected, in particular not inhibited.

An aqueous reaction medium may also contain further constituents, as for example buffer constituents, in order to further favour a reaction to be performed according to the present invention.

"Regeneration" of a cofactor refers to the partial or complete reconstitution of the active form of the cofactor, as required for performing a particular enzymatic reaction, which otherwise would consume said active cofactor. Said regeneration may be performed simultaneously with said enzymatic reaction, i.e. may be coupled to said enzymatic reaction, or may be performed stepwise.

A "hydrolysis" of an ester may be catalyzed by an enzyme, as for example an esterase enzyme, or by applying a suitable pH value, as for example, by adjusting the pH value to a value in the basic pH range above pH 7.

2. Proteins Used According to the Invention

The present invention is not limited to the specifically mentioned proteins, but also extends to functional equivalents thereof.

"Functional equivalents" or "analogs" or "functional mutations" of the concretely disclosed enzymes are, within the scope of the present invention, various polypeptides thereof, which moreover possess the desired biological function or activity, e.g. enzyme activity.

For example, "functional equivalents" means enzymes, which, in a test used for enzymatic activity, display at least a 1 to 10%, or at least 20%, or at least 50%, or at least 75%, or at least 90% higher or lower activity of an enzyme, as defined herein.

"Functional equivalents", according to the invention, also means in particular mutants, which, in at least one sequence position of the amino acid sequences stated above, have an amino acid that is different from that concretely stated, but nevertheless possess one of the aforementioned biological activities. "Functional equivalents" thus comprise the mutants obtainable by one or more amino acid additions, substitutions, deletions and/or inversions, where the stated changes can occur in any sequence position, provided they lead to a mutant with the profile of properties according to the invention. Functional equivalence is in particular also provided if the reactivity patterns coincide qualitatively between the mutant and the unchanged polypeptide, i.e. if for example the same substrates are converted at a different rate. Examples of suitable amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxy groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent enzymes can be determined on the basis of the concrete parameters of the invention.

"Functional equivalents" also comprise fragments, preferably individual domains or sequence motifs, of the polypeptides according to the invention, which for example display the desired biological function.

"Functional equivalents" are, moreover, fusion proteins, which have one of the polypeptide sequences stated above or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" that are also included according to the invention are homologues of the concretely disclosed proteins. These possess percent identity values as stated above. Said values refer to the identity with the concretely disclosed amino acid sequences, and may be calculated according to the algorithm of Pearson and Lipman, Proc. Natl. Acad, Sci. (USA) 85(8), 1988, 2444-2448. The % identity values may also be calculated from BLAST alignments, algorithm blastp (protein-protein BLAST) or by applying the Clustal setting as given below.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13): 3497-500, and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

A percentage identity of a homologous polypeptide according to the invention means in particular the percentage identity of the amino acid residues relative to the total length of one of the amino acid sequences concretely described herein.

In the case of a possible protein glycosylation, "functional equivalents" according to the invention comprise proteins of the type designated above in deglycosylated or glycosylated form as well as modified forms that can be obtained by altering the glycosylation pattern.

Such functional equivalents or homologues of the proteins or polypeptides according to the invention can be produced by mutagenesis, e.g. by point mutation, lengthening or shortening of the protein.

Such functional equivalents or homologues of the proteins according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues (Arkin and Yourvan (1992) PNAS 89:7811-7815; Delgrave et al. (1993) Protein Engineering 6(3):327-331).

3. Further Embodiments of the Claimed Methods 3.1. General

The methods of the invention can be carried out batchwise, semibatchwise or continuously.

The enzyme or enzymes, which may be present during the a method of the invention can be present in living cells producing the enzyme or enzymes, in harvested cells, in dead cells, in permeabilized cells, in crude cell extracts, in partially purified extracts, or in essentially (approx. 90-99.5 wt-%) or completely (approx. 99.5-99.9 wt-%, or 100 wt.-%) (each per total dry weight of the enzyme preparation) pure form.

The enzymes may be appied in free or immobilized. An immobilized enzyme is fixed to a suitable inert carrier. Suitable carriers are for example described in EP-A-1149849, EP-A-1 069 183 and DE-OS 100193773 as well as further documents referenced therein. Suitable carriers are, for example clays, like kaolinite, perlite, silicion dioxide, aluminium oxide, sodium carbonate, calcium carbonate, cellulose powder, anion exchangers, synthetic polymers, like polystyrene, acrylic resins, phenolformaldehyde resins, polyurethanes and polyolefins, like polyethylenes and polypropylenes. Carriers are normally used in particulate, preferentially porous form. Particle sizes are normally in the range of not more than 5 mm, or not more than 2 mm. Enzymes or cells may also be cross-linked with glutaraldehyde. Suitable immobilization techniques are, for example described in J. Lalonde and A. Margolin "Immobilization of Enzymes" "in K. Drauz and H. Waldmann, Enzyme Catalysis in Organic Synthesis 2002, Vol. III, 991-1032, Wiley-VCH, Weinheim.

The methods according to the invention can be performed in common reactors, which are known to those skilled in the art, and in different ranges of scale, e.g. from a laboratory scale (few milliliters to dozens of liters of reaction volume) to an industrial scale (several liters to thousands of cubic meters of reaction volume).

If enzymes are used in immobilized form a reactor can be used. The reactor usually allows controlling the amount of the at least one enzyme, the amount of the at least one substrate, the pH, the temperature and the circulation of the reaction medium. When the at least one enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for upscaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Aufl., R. Oldenbourg Verlag, München, Wien, 1984; or in Biotechnology, Volume 3, 2nd Edition, Rehm et al. Eds., (1993), in particular Chapter II).

Cells containing the at least one enzyme of the invention can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecyl-maltoside, octylglycoside, Triton® X-100, Tween® 20, deoxycholate, CHAPS (3[(3-Cholamidopropyl)dimethylammonio]-1-propansulfonate), Nonidet® P40 (Ethylphenolpoly(ethyleneglycolether), and the like.

Suitable enzyme contents may be determined easily by a skilled person by performing a limited number of optimization experiments.

3.2 pH Values and Buffers 3.2.1 Oxidation Step a)

In the method of the invention, enantiomerically pure or chiral substrates in pure form or as mixtures of stereoisomers which show enrichment of one steremer may be applied.

The conversion of a substrate according to the general formula (1) into aminoaldehyde according to the general formula (2) is usually performed at a pH from about 6.0 to about 10.0, as for example at a pH from about 7 to 9.5, depending on the optimum conditions for the enzyme (dehydrogenase or oxidase) or enzyme system (combination with cofactor regenerating enzymes). The pH optimum can be determined easily by means of a limited number of routine experiments in advance. For example the pH is in the range from 6.5 to 7.5, more particular in the range from about 7.0. if an alcohol oxidase of *Pichia pastoris* is applied. Alternatively the alcohol dehydrogenase from *Equus caballus* requies a more alkaline pH and the reaction may be performed in the range of about 8.5 to 9.5 more particular in the range from about 9.0.

Any buffer suitable for the aforementioned pH values or pH ranges can be used, e.g. MOPS, HEPES, PIPES, phosphate, borate and Tris buffers. In a pH range from 7.5 to 9.0 Tris buffers may be applied, while phosphate or MOPS buffers may be applied in a pH range from 6.0 to 8.0. The concentration of the buffer may be varied depending on the process conditions and may be in the range from 1 mM to 200 mM, e.g. 1 mM to 100 mM, 1 mM to 50 mM. In particular the buffer concentration may be from 2 mM to 25 mM or 3 mM to 10 mM, such as 5 mM.

3.2.2 Polyimine Formation Step b)

In order to induce polymerization, the pH of the reaction medium is lowered by adding a suitable inorganic or organic acid. For example, inorganic acids like $H_2SO_4$, or HCl, may be added. The pH will be lowered to reach a range which supports polymerization of the aminoaldehyde monomers. Usually said pH may be in the range of about 3.5 to 5.5, in particular 4 to 5. The acid may be added to the reaction mixture as obtained from step a) or may also be performed with the reaction mixture of step a) after having removed one or more constituents thereof, as for example proteinaceous material resulting from enzyme deactivation, which occurs either gradually or by the addition of suitable inactivating agents, like EDTA or hydrogen peroxide, or by removing nonconverted reactants or co-reactants required for the cofactor regeneration. Usually, however, no pre-treatment is required for performing step b).

3.2.3 Reduction Step c)

Reduction may be performed either subsequently to or simultaneously with step b). A reducing agent suitable for reducing said polyimine in aqueous solution to the corresponding polyamine, as for example sodium cyanoborohydrine, or sodium borohydride, sodium triacetoxyborohydride, $H_2$/PdC is added in sufficient quantity to provide for the desired degree (preferably complete) hydrogenation of the imine groups. For example the reducing agent may be added in a 2 to 10-fold molar excess.

3.2.4 $NAD(P)^+$ Cofactor Regeneration

The pH and buffer conditions suitable for cofactor regeneration may be substantially identical with those for step a) above in case cofactor regeneration is coupled to such an aminoaldehyde formation step a). In case of coupling with other cofactor consuming redox enzymes and different substrates a skilled reader will appreciate that then the specific process conditions may be adapted to the new system, which can be achieved by a limited number of routine experiments.

3.3. Reaction Temperature and Duration

The method steps of the invention can be performed at any temperature which is tolerable for the applied enzymes or assists the intended chemical or enzymatic conversion reaction used.

The temperature for the enzymatic conversions may correlate with the optimal growth temperatures of the organisms or microorganism harbouring the enzyme(s) or used as source for their extraction, but can easily determined by those skilled in the art.

In general, the method steps can be performed at temperatures from 20° C. to 70° C., in particular from 40° to 50° C. Examples for reaction temperatures are about 30° C., about 35° C., about 37° C., about 40° C., about 45° C., about 50° C., about 55° C. and about 60° C.

Each step may proceed until an equilibrium between the substrate and the corresponding product is achieved, but may be stopped earlier. Usual reaction times are in the range from about 1 minute to 25 hours, in particular about 10 min to 6 hours or in the range from about 1 hour to 4 hours.

3.4 Cosolvents

If necessary, in order to increase the solubility of substrates one or more organic co-solvent(s) can be included in the reaction medium. Examples for suitable cosolvents are butane-2-ol, methyl-tert-butyl ether (MTBE) and dimethylsulfoxide (DMSO). For said co-solvents, a concentration below the saturation in aqueous medium may be applied, e.g. about 6% or less, about 5% or less, about 4% or less, about 3% or less, about 2% or less, or about 1% or less.

3.5 Other Reactants

Further reactants or co-reactants required for performing a reaction of the present invention (conversion of substrate, cofactor regeneration) may be added as necessary and at suitable amounts to the reaction system.

For example, cofactor $(NAD(P)^+)$ may be added in non-stoichiometric amount as for example in a range of 0.001 to 10, 0.01 to 5 or 0.1 to 1 mM For example, activated esters for cofactor regeneration, like vinyl acetate may be added in suitable amounts, as for example in a range of 1 to 10 or 2 to 5 times molar excess compared to amino alcohol.

For example, hydrogen peroxide may be added in suitable amounts, as for example in a range of 0.0001 to 10, 0.001 to 10, 0.01 to 5 or 0.1 to 1 mM 3.6 Polymer Isolation The methodology of the present invention can further include a step of polymer recovering. The term "recovering" includes extracting, harvesting, isolating or purifying the compound from the reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, lyophilization and the like and combinations thereof.

For example the polymer can be recovered from reaction by first removing residual microorganisms or proteins, or, if substantially no such impurities are anymore present, by reducing solubility of the polymer in aqueous environment and (optionally repeated) extraction with a suitable organic, preferably substantially water-insoluble solvent Suitable solvents are for example, dichloromethane, toluene, methylene chloride, butyl acetate, diisopropyl ether, benzene, MTBE or ethyl acetate, without being limited thereto.

Extraction may be performed after having increased the pH of the mixture to about pH 12 to 14, by adding a suitable base, like NaOH and adjusting the ionic strength, for example by adding aqueous salt solution like brine.

The following examples only serve to illustrate the invention. The numerous possible variations that are obvious to a person skilled in the art also fall within the scope of the invention.

EXPERIMENTAL PART

Example 1

Polyamine Preparation in Aqueous Medium by Means of Horse Liver Alcohol Dehydrogenase (HLADH) or Alcohol Oxidase (AOX)

Figure 2:
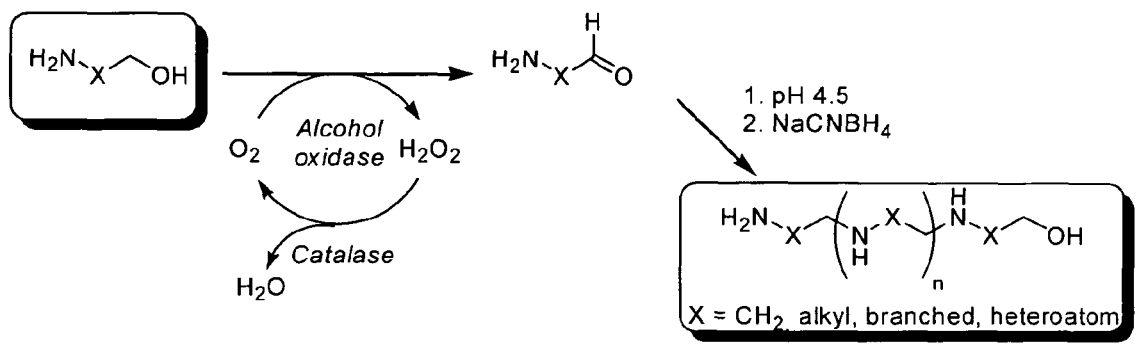
FIG. 2: Schematic representation of polyamine synthesis catalyzed by an alcohol oxidase. The pH is lowered to pH 4.5 allowing polyimine formation. This is then followed by reduction of the polyimine by cyanoborohydride. The enzyme utilizes oxygen and formed hydrogen peroxide is further oxidized in situ by catalase.

Said two different approaches for polyamine synthesis in aqueous medium are schematically illustrated in FIG. 1 and FIG. 2.

In the HLADH approach cofactor regeneration is accomplished by the use of vinyl acetate. Vinyl acetate rapidly hydrolyzes at pH 9.1, decomposing into acetic acid and acetic aldehyde. The aldehyde can be reduced by HLADH into ethanol, thereby forming $NAD^+$ from NADH. Unreacted acetic aldehyde can be removed by bubbling $N_2$ after deactivating the enzyme with EDTA or $H_2O_2$. For the alcohol dehydrogenase HLADH the reaction was spectrophotometrically followed by the formation of NADH at 340 nm. Different concentrations of the various amino alcohols were used to obtain the Michaelis-Menten kinetic constants.

In the AOX approach cofactor regeneration is not required. The reaction is further driven by the Catalase-catalyzed decomposition of hydrogen peroxide. The AOX reaction may be assayed spectrophotometrically by following the formation of hydrogen peroxide by addition of peroxidise and 2,2'-azino-bis(3-ethylbenzthiazoline-6-sulphonic acid) (ABTS) at 420 nm.

a) Materials

Chemicals as used for the present experiments were of >98% purity grade and were purchased from Sigma Aldrich.

The AOX used (*Pichia pastoris*) had no activity for aminoalcohols at alkaline pH, therefore the synthesis was performed at pH 7.0. The enzyme was obtained from commercially available from Sigma Aldrich.

The alcohol dehydrogenase (*Equus caballus*) did not show any activity at neutral pH but had good reaction rates at alkaline pH. This reaction was performed at pH 9.1. The enzyme was obtained from commercially available from Sigma Aldrich.

b) Polyamine Syntheses b1) Polyamine Synthesis with AOX

An amino alcohol selected from 3-amino propanol, D-alaninol, L-alaninol or 2-phenyl glycinol, was dissolved in 100 mM MOPS-buffer to concentrations between 5 mM to 3 M, in volumes between 1 mL and 300 mL, and the pH was set to 7.0 with HCl. AOX and Catalase was added and the solution was incubated at 25° C. for 48 h. The amount of AOX was adjusted to the required amount for complete conversion within 24 h, with an at least 10 times enzymatic unitary excess of Catalase. Addition of acetic acid lowered the pH to 4.5, and 3 equivalents of $NaCNBH_3$ were added.

b2) Polyamine Synthesis with HLADH

An amino alcohol was dissolved in water, 1 mL to 300 mL, to concentrations between 5 mM and 3 M together with vinyl acetate at double molar excess, and the pH was set to 9.1 with NaOH/HCl, the substrates themselves have buffering capacity at this pH. ADH (alcohol dehydrogenase) and $NAD^+$ (0.5 mM) was added and the solution was incubated for 48 h at 25° C. The enzyme amount was adjusted to achieve complete conversion in 24 h.

Thereafter, 30% $H_2O_2$ was added to a peroxide concentration of 100 equivalents to enzyme and the reaction was incubated for 4 h. The acetic aldehyde was removed by bubbling $N_2$ through a syringe immersed in the mixture for 4 h. The pH was then lowered to 4.5 by addition of HCl, and 3 equivalents of $NaCNBH_3$ was added.

c) Extraction of Product

The reaction mixture was mixed with one equivalent of brine and the pH was set to 14 by addition of NaOH. Repeated shaking with dichloromethane was thereafter used to separate the polymer/oligomer from the aqueous solution. The dichloromethane-phase was thereafter subjected to lyophilisation leaving a viscous material which is the oligo/polyamine.

d) Characterization

The material (produced poly/oligomer) was dissolved in dimethylsulphoxide and subjected to size exclusion chromatography (SEC).

Alternatively, different amounts, ranging from 1 µL to 200 µL, of material (produced poly/oligomer) was dissolved in a 0.5 mL acetonitrile/water (1:1)-solution with 3% trifluoroacetic acid and 10 g/L 2,5-dihydroxy benzoic acid and subjected to mass spectrometry by means of matrix assisted laser desorption ionisation (MALDI) where the ionic masses were measured by time of flight (TOF).

e) Results and Discussion

The molecular weight of the polyamine compound is dependent on the extent of the formation of aminoaldehyde. For the reaction with HLADH an excess of vinyl acetate was added for obtaining complete conversion of substrate, the formed acetic aldehyde was removed by bubbling $N_2$ through the mixture. With AOX, dissolution of oxygen from ambient air and the action of Catalase ensures complete conversion.

To form the imines the pH is lowered to 4.5 by addition of acetic acid and/or HCl. The formed acetic acid from the hydrolysis of the activated ester, when using alcohol dehydrogenase, functions as a buffer at this pH, so HCl can be used in this case.

The results for the conversion of different aminoalcohols catalysed by AOX are summarized in Table 1 which also shows the kinetic constants.

TABLE 1

Kinetic constants for AOX, pH 7.0, 100 mM MOPS-buffer.

| Substrate | $K_M$ (mM) | $V_{max}$ ($\mu mol*min^{-1}*mg^{-1}$) | Relative activity (%) | E-value |
|---|---|---|---|---|
| 2-Amino-ethanol | — | Very low | ~0 | |
| 3-Amino-propan-1-ol | 400 | 0.021 | 0.18 | |
| R-2-Amino-propan-1-ol | 300 | 0.10 | 0.88 | 3.6 |
| S-2-Amino-propan-1-ol | 250 | 0.37 | 3.2 | |
| R-2-Amino-1-phenyl-ethanol | — | Unknown | — | Rate similar to 2-amino-propan-1-ol |
| S-2-Amino-1-phenyl-ethanol | — | Unknown | — | |
| 1-Amino-propan-2-ol (rac) | — | — | 0 | |
| Ethanol | 1.3 | 12 | 100 | |

Reaction followed spectrophotometrically at 420 nm via the formation of hydrogen peroxide by addition of peroxidase and ABTS.

E-value=the proportional preference of one enantiomer over the other as substrate, as defined by the division of the specificity constants. The specificity constant is defined as $k_{cat}/K_m$.

For 2-Amino-1-phenyl ethanol (2-phenyl glycinol) the assay could not be used since the substrate precipitates upon addition of ABTS. Other experiments wherein the ABTS had been replaced by pyrogallol or purpald were used to measure formation of aldehyde, were inconclusive. However, the experiments did indeed show that the enzyme was catalysing the reaction and the appearance of aldehyde. The reproducibility of the rates in these experiments was not satisfactory; hence no kinetic data could be extracted.

The results for the conversion of different aminoalcohols catalysed by HLADH are summarized in Table 2 which also shows the kinetic constants.

TABLE 2

Kinetic constants for HLADH, pH 9.1, 100 mM CHES-buffer.

| Substrate | $K_M$ (mM) | $V_{max}$ ($\mu mol*min^{-1}*mg^{-1}$) | Relative activity (%) | E-value |
|---|---|---|---|---|
| 2-Amino-ethanol | — | <0.005 | ~0 | |
| 3-Amino-propan-1-ol | 13 | 0.17 | 11 | |
| R-2-Amino-propan-1-ol | — | <0.0007 | ~0 | >300 |
| S-2-Amino-propan-1-ol | 6.3 | 0.21 | 14 | |
| R-2-Amino-1-phenyl-ethanol | — | <0.002 | ~0 | >100 |
| S-2-Amino-1-phenyl-ethanol | 6.2 | 0.21 | 14 | |
| 1-Amino-propan-2-ol (rac) | — | 0 | 0 | |
| Ethanol | 0.60 | 1.5 | 100 | |

Reaction catalysed by HLADH was followed spectrophotometrically at 340 nm, by the formation of NADH.

Figure 3:
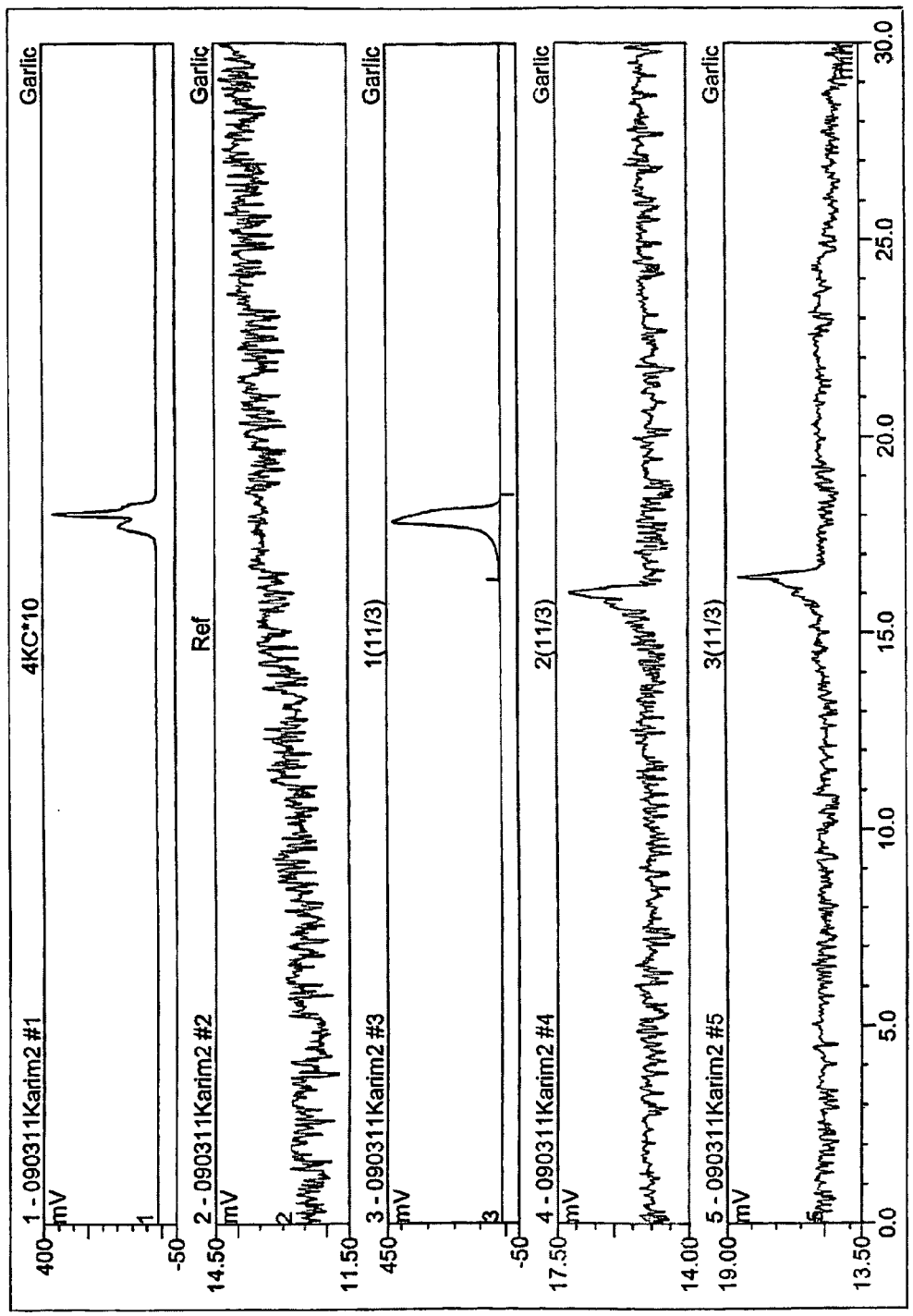
FIG. 3: Size exclusion chromatograms. From the top: Polymer made from 2-phenyl glycinol, Reference (PEI1800) which did not work (perhaps it was overloaded), polymer made from 3-amino propanol, polymer made from D-alaninol, polymer made from L-alaninol. Each of the Polymers has am molecular weight of about 1000 Da (Mw standards not shown)

After extraction with dichloromethane (the aqueous solution was mixed with one equivalent of brine and the pH was set to 14), and after evaporation of solvent the material could be subjected to size exclusion chromatography (SEC) after dissolution in DMSO. FIG. 3 shows the chromatograms.

The polydispersity was estimated to vary between 1.04 and 1.07 (Done by the software, Millenium).

Figure 4:
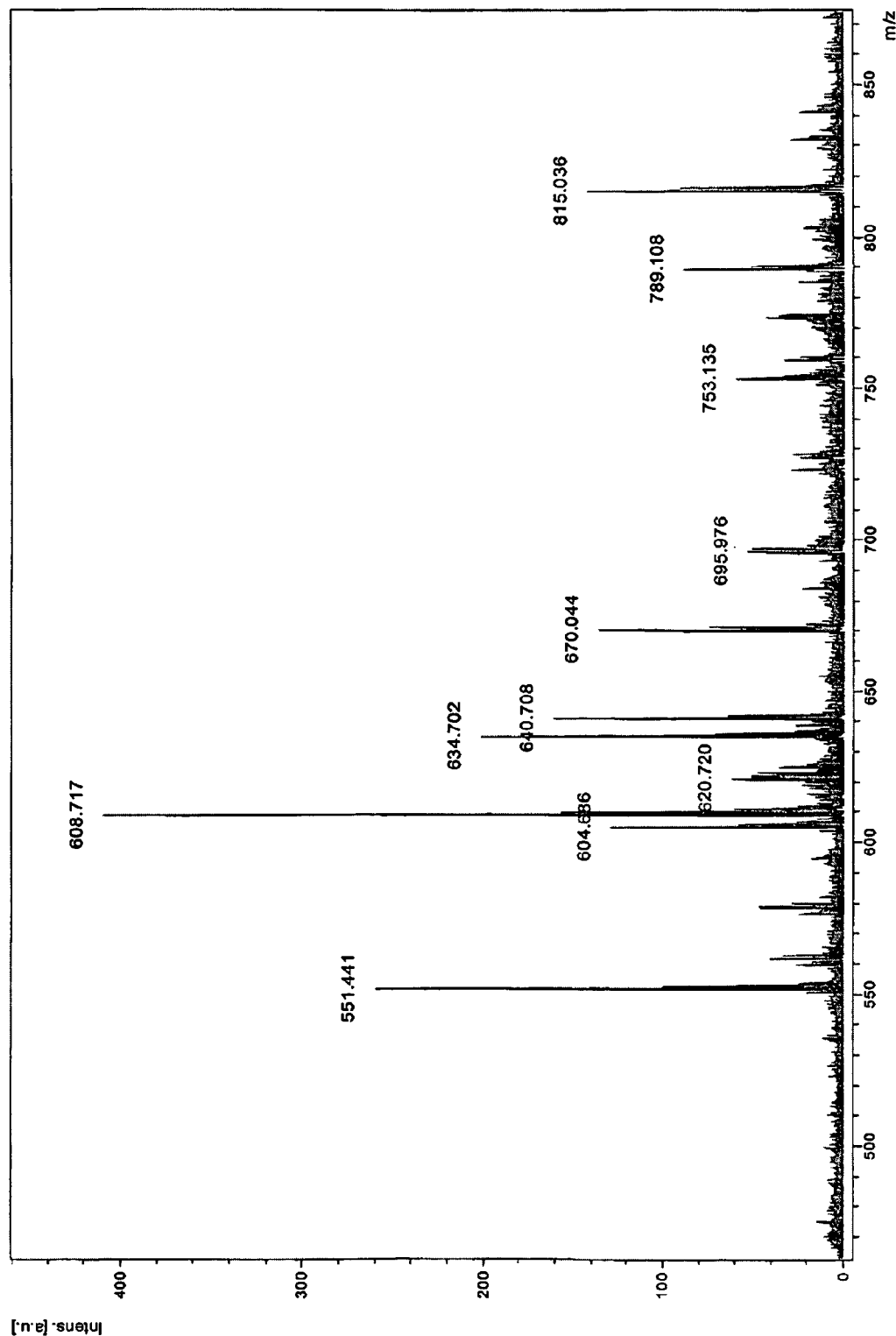
FIG. 4: MALDI-TOF spectrum of the oligomer formed from 2-phenyl glycinol.

The extracted material could also be subjected to mass spectrometry. The material was dissolved in water/acetonitrile 1:1 with 3% TFA and 10 g/L 2,5-dihydroxybenzoic acid, at varying concentrations. A spectrum of the polymer formed from 2-phenyl glycinol is shown in FIG. 4.

The presence of subunits without phenyl groups are assumed to be present and originate from contaminations in the starting material. If alaninol is present as a contaminant and is a better substrate than the 2-phenyl glycinol, it would be incorporated before the remaining molecules are converted to aldehyde. Such subunits correspond to a mass difference of 57.06, whereas the subunits with phenyl groups correspond to a mass difference of 119.07. These mass differences can be used to explain the difference in masses of the peaks in the spectrum of FIG. 4.

Figure 5:
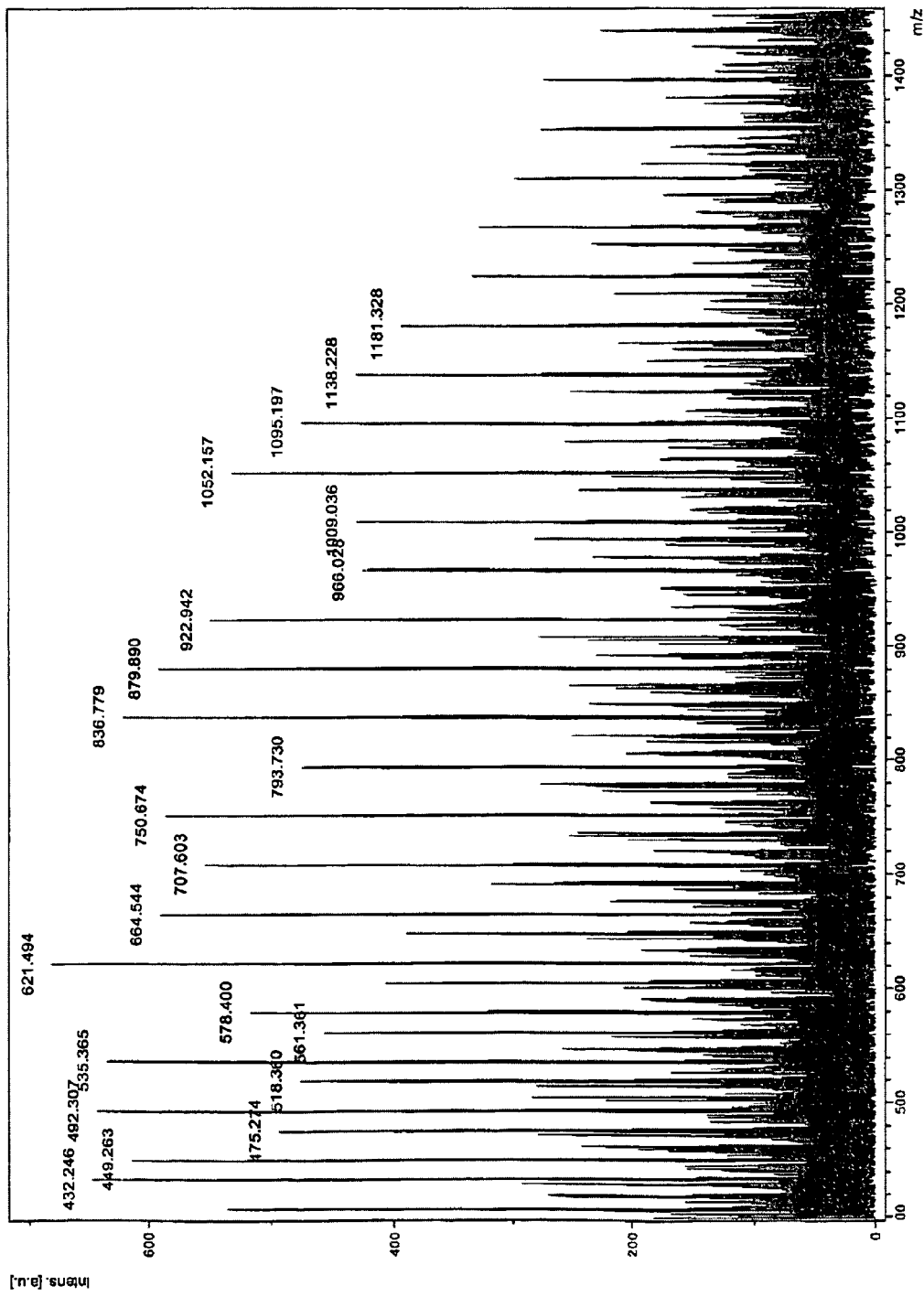
FIG. 5: MALDI-TOF spectrum of PEI1800.

Commercial PEI1800 was also tested on the MALDI-TOF, the spectrum is presented in FIG. 5. In FIG. 5 there are several series of polymer present, giving rise to a rather unclear spektrum. The mass difference between the peaks is approximately 43 as expected.

The invention claimed is:

1. A process for the production of a polyamine of the formula (4)

wherein
n is an integer of at least 1;
residues X independently of each other represent a linear or branched, saturated or unsaturated, hydrocarbylene residue;
residues R independently of each other represent a hydrogen atom or a linear or branched, saturated or unsaturated, hydrocarbyl residue; and
wherein the terminal $H_2N-$ and $HO-CH_2-$ groups may be condensed to form an intramolecular amino linkage;
comprising the steps of
a) enzymatically oxidizing an aminoalcohol of the general formula (1), which may be chiral or non-chiral, and may be applied in optically pure form or as a mixture of isomers, to the corresponding aminoaldehyde of the formula (2)

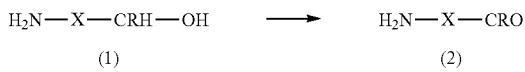

wherein X and R are as defined above;
b) allowing the aminoaldehyde of the formula (2) to polymerize to form a polyimine (3),

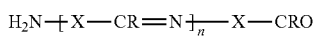

wherein X, R and n are as defined above; and
c) reducing the polyimine of the formula (3) to the corresponding polyamine of the formula (4).

2. The process according to claim 1, wherein the aminoalcohol of step a) is a compound of the formula (1), wherein $X=-CH_2-CH_2-$.

3. The process according to claim 1, wherein at least one residue X carries one or more identical or different heteroatoms selected from N, O, and S.

4. The process according to claim 1, wherein at least one residue R carries one or more heteroatoms selected from N, O, and S.

5. The process according to claim 1, wherein the enzyme of step a) is selected from dehydrogenases and oxidases.

6. The process according to claim 5, wherein the enzyme of step a) is selected from the group consisting of alcohol dehydrogenase E.C. 1.1.1.1, alcohol dehydrogenase (NADP$^+$) 1.1.1.2, allyl-alcohol dehydrogenase E.C. 1.1.1.54, alcohol dehydrogenase [NAD(P)$^+$] E.C. 1.1.1.71, aryl-alcohol dehydrogenase E.C. 1.1.1.90, aryl-alcohol dehydrogenase (NADP$^+$) E.C. 1.1.1.91, 3-hydroxybenzyl-alcohol dehydrogenase E.C. 1.1.1.97, perillyl-alcohol dehydrogenase E.C. 1.1.1.144, long-chain-alcohol dehydrogenase E.C. 1.1.1.192, coniferyl-alcohol dehydrogenase E.C. 1.1.1.194, cinnamyl-alcohol dehydrogenase E.C. 1.1.1.195, cyclohexanol dehydrogenase E.C. 1.1.1.245, 4-(hydroxymethyl)benzenesulfonate dehydrogenase E.C. 1.1.1.257, 3-methylbutanal reductase E.C. 1.1.1.265, S-(hydroxymethyl)glutathione dehydrogenase E.C. 1.1.1.284, alcohol dehydrogenase (acceptor) E.C. 1.1.99.8, polyvinyl-alcohol dehydrogenase (acceptor) E.C. 1.1.99.23, formaldehyde dehydrogenase (glutathione) E.C. 1.2.1.1 and alcohol oxidase, E.C. 1.1.3.13, aryl-alcohol oxidase E.C. 1.1.3.7, secondary-alcohol oxidase E.C. 1.1.3.18, long-chain-alcohol oxidase E.C. 1.1.3.20, polyvinyl-alcohol oxidase E.C. 1.1.3.30 and vanillyl-oxidase E.C. 1.1.3.38.

7. The process according to claim 5, wherein in step a) NAD$^+$ is used as a cofactor for the oxidation if an alcohol dehydrogenase is applied; or the reaction is performed aerobically if an alcohol oxidase is applied.

8. The process according to claim 7, wherein the NAD$^+$ cofactor is regenerated enzymatically by the reduction of an aldehyde or ketone to the corresponding alcohol by the same dehydrogenase enzyme.

9. The process of claim 7, wherein the aldehyde or ketone are formed by a hydrolysis of an activated ester.

10. The process according to claim 1, wherein the chemical reduction step c) is performed in the presence of NaBH$_3$CN or Pd/H$_2$.

11. The process according to claim 1, wherein a polyamine in the molecular range of Mn=100 to 7,000,000 is obtained.

12. The process according to claim 1, wherein step b) is performed in an aqueous medium having a pH supporting the formation of polyimine.

13. The process according to claim 12, wherein the aqueous medium has a pH in the range of 3.5 to 6.

14. The process according to claim 1, wherein step a) is performed in an aqueous medium having a pH in the range of 6 to 10.

15. The process according to claim 1, wherein the enzyme is used in dissolved, dispersed or immobilized form.

16. A process for the production of a polyamine of the formula (4)

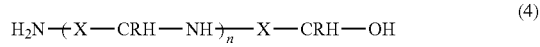

wherein
n is an integer of at least 1;
residues X independently of each other represent a linear or branched, saturated or unsaturated, hydrocarbylene residue;
residues R independently of each other represent a hydrogen atom or a linear or branched, saturated or unsaturated, hydrocarbyl residue; and
wherein the terminal $H_2N-$ and $HO-CH_2-$ groups may be condensed to form an intramolecular amino linkage;

comprising the steps of a) enzymatically oxidizing an aminoalcohol of the formula (1), which may be chiral or non-chiral, and may be applied in optically pure form or as a mixture of isomers, to the corresponding aminoaldehyde of the formula (2)

wherein X and R are as defined above;

b) allowing the aminoaldehyde of the formula (2) to polymerize to form a polyimine (3),

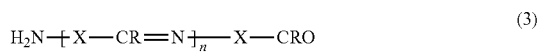

wherein X, R and n are as defined above; and
reducing the polyimine of the formula (3) to the corresponding polyamine of the formula (4);
wherein the enzyme is a horse liver alcohol dehydrogenase (HLADH) and has the amino acid sequence of SEQ ID NO:1 or an alcohol oxidase having a amino acid sequence of SEQ ID NO:2; or a mutant or variant thereof having a sequence identity of at least 90% to a sequence of SEQ ID NO: 1 or 2.

* * * * *